US007332503B2

(12) United States Patent
Wikstrom et al.

(10) Patent No.: US 7,332,503 B2
(45) Date of Patent: *Feb. 19, 2008

(54) APORPHINE ESTERS AND THEIR USE IN THERAPY

(75) Inventors: Hakan Wikstrom, Groningen (NL); Durk Dijkstra, Bedum (NL); Thomas Cremers, Groningen (NL); Per Erik Andren, Uppsala (SE); Sandrine Marchais, Groningen (NL); Ulrik Jurva, Groningen (NL)

(73) Assignee: Axon Biochemicals B.V., Groningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/061,881

(22) Filed: Feb. 22, 2005

(65) Prior Publication Data

US 2005/0143408 A1 Jun. 30, 2005

Related U.S. Application Data

(63) Continuation of application No. 10/344,420, filed as application No. PCT/SE01/01658 on Jul. 20, 2001.

(30) Foreign Application Priority Data

Aug. 17, 2000 (SE) .................................... 0002934

(51) Int. Cl.
*A61K 31/473* (2006.01)
*C07D 221/18* (2006.01)
(52) U.S. Cl. ........................................ 514/284; 546/75
(58) Field of Classification Search ................ 514/284; 546/75
See application file for complete search history.

(56) References Cited

U.S. PATENT DOCUMENTS 4,080,456 A    3/1978   Seidelmann et al.
4,279,914 A    7/1981   Maasbol et al.
2004/0018956 A1 1/2004  Wikstrom et al.

FOREIGN PATENT DOCUMENTS

| EP | 0 040 074 | 11/1981 |
| FR | 2 373 530 | 7/1978 |
| WO | 97/06786 | 2/1997 |
| WO | 98/31368 | 7/1998 |
| WO | 99/62502 | 12/1999 |
| WO | WO 00/03698 | 1/2000 |
| WO | WO 00/69416 | 11/2000 |
| WO | 02/14279 | 2/2002 |

OTHER PUBLICATIONS

STN International, File Caplus Caplus accession No. 1981:47565, document No. 94:47565 J.F. Green et al.: "Aporphones. XXVI: GLC and mass spectrometic properties of trifluoroacetyl derivatives of N-methyl, N-propyl-, and noraporphines".
STN International, File Caplus Caplus accession No. 1978:70, document No. 88:70 D. Michael Baaske et al.: "Gas chromatogrpahic determination of apomorphine in plasma".
Nobutoshi Watari et al.; "Nonlinear Assessment of Nitrofurantoin Bioavailability in Rabbits", Journal of Pharmacokinetics and Biopharmaceutics, vol. 11, No. 5, pp. 529-545: 1983.
J.F. Green, et al., "Aporphines XXVI: GLC and Mass Spectrometric Properties of Trifluoroacetyl Derivatives of N-Methyl-N-Propyl-, and Noraporphines", Journal of Pharmaceutical Sciences, vol. 69, No. 8, Aug. 1980, pp. 936-942.
D.M. Baaske, et al., "Gas Chromatographic Determination of Apoorphine in Plasma", Journal of Chromatography, 140, 1977, pp. 57-64.

*Primary Examiner*—Charanjit S. Aulakh
(74) *Attorney, Agent, or Firm*—Oblon, Spivak, McClelland, Maier & Neustadt, P.C.

(57) ABSTRACT

New aporphine derivatives are disclosed which have formula (I) and the physiologically acceptable salts thereof. Said derivatives may be used for the treatment of Parkinson's disease, hemicrania, restless legs syndrome (RLS), sexual dysfunction in men and women, hyperprolactemia and psychotic disorders, and/or evaluation of Parkinson's disease. Processes for the preparation of such derivatives are also disclosed.

28 Claims, No Drawings

APORPHINE ESTERS AND THEIR USE IN THERAPY

CROSS-REFERENCE TO RELATED APPLICATIONS

The present application is a continuation of U.S. application Ser. No. 10/344,420, filed on Jul. 15, 2003, which is a National Stage (371) of application Ser. No. PCT/SE01/01658, filed on Jul. 20, 2001, the contents of which are incorporated herein by reference.

FIELD OF THE INVENTION

This invention relates to new aporphine esters, a process for their preparation, pharmaceutical compositions containing them and their use in therapy. More particularly, the present invention relates to new aporphine 10- and 11-monoesters and 10,11-asymmetric di-esters, their preparation and use and pharmaceutical compositions containing them.

BACKGROUND ART

Parkinson's disease is a progressive, neurodegenerative disorder caused by a loss of the cell bodies of dopaminergic (DA-ergic) neurons from the substantia nigra and degeneration of nerve terminals in the striatum resulting in low levels of DA in the substantia nigra and corpus striatum. Parkinson's disease is characterized by chronic, progressive motor dysfunction and its main symptoms are tremor at rest, muscle rigidity and a decrease in the frequency of voluntary movements (hypokinesia) with difficulty in stopping, starting and turning when walking. A persistent tremor is superimposed on hypertonicity of opposing muscle groups and initiation of movements becomes increasingly difficult and slow. In advanced stages, patients' movements become virtually "frozen", and patients are unable to care for themselves. Studies have shown that the symptoms of Parkinson's disease appear when the striatal DA content is reduced to 20-40% of normal.

As Parkinson's disease is associated with a loss of DA from the striatum, it is commonly treated with drugs which replace DA, the most commonly used of these being levodopa. Levodopa is converted by dopa decarboxylase into DA in the brain and it is this DA which exerts a therapeutic effect. However, although levodopa is well absorbed from the small intestine, much of it is inactivated by monoamine oxidase in the wall of the intestine. Also, the plasma half-life of levodopa is short and about 95% of the drug is converted to DA in pripheral tissues, where dopa decarboxylase is widespread, with the result that less than 1% enters the brain. Consequently levodopa has to be administered in large and frequent doses. In addition, the production of DA in peripheral tissues gives rise to unwanted side-effects.

Accordingly, levodopa is normally given in combination with other drugs to enhance the effects of levodopa in the brain and minimize its peripheral effects. In particular, levodopa is usually given in combination with a peripheral dopadecarboxylase inhibitor, which cannot cross the blood-brain barrier, such as carbidopa, which inhibits the breakdown of levodopa to DA outside the brain, thereby reducing peripheral unwanted effects. The inhibitor also ensures that a relatively large amount of an oral dose of levodopa reaches the brain and thus enables the dose of levodopa to be reduced which also reduces peripheral side-effects. In addition, a peripheral DA antagonist, which does not penetrate the blood-brain barrier, such as domperidone, may also be administered to reduce the nausea and vomiting side-effects of levodopa.

In addition to the side-effects mentioned above, further undesirable effects are associated with the prolonged use of levodopa. In particular, many patients develop involuntary choreiform movements, which are the result of excessive activation of DA receptors. These movements usually affect the face and limbs and can become very severe. Such movements disappear if the dose of levodopa is reduced but this causes rigidity to return. Moreover, the margin between the beneficial and the unwanted effect appears to become progressively narrower as the period of levodopa treatment increases. The traditional method of combating this effect is to increase the frequency of administration of levodopa whilst keeping the overall dose steady. This approach reduces end-of-dose deterioration and diminishes the likelihood of the patient developing the dyskinesias that occur with high peak doses.

A further complication of long-term levodopa treatment is the development, of rapid fluctuations in clinical state where the patient switches suddenly between mobility and immobility for periods ranging from a few minutes to a few hours. This phenomenon is known as the "on-off effect", the "on" state being the preferred state during which nearly normal motor functioning can be attained, and the "off" state being characterized by dystonic postures during periods of decreased mobility. Indeed, this effect can produce such an abrupt loss of mobility that the patient may suddenly stop while walking or be unable to rise from a chair in which he had sat down normally a few moments earlier. This effect is commonly unaffected by manipulation of the dose of levodopa and may require treatment with alternative drugs. In addition to the above long-term side-effects of levodopa treatment, it has been found that the effectiveness of levodopa gradually declines with time until it is no longer effective. Also, an increased incidence of malignant melanoma has been observed in patients undergoing; treatment with levodopa and it has therefore been suggested that treatment with levodopa may be linked with the development of malignant melanoma. Accordingly, the use of levodopa in the treatment of Parkinson's disease is far from ideal.

An alternative approach to the treatment of Parkinson's disease is the use of drugs that mimic the action of DA. Such drugs are collectively known as DA agonists because they directly stimulate DA receptors within the DA-deficient nigro-striatal pathway. Unlike levodopa, DA agonists do not need to be converted in the brain to active compounds. Also, DA agonists are effective in patients in the advanced stages of Parkinson's disease when levodopa is no longer effective because they act directly on the DA receptors and are therefore unaffected by the lack of DA-producing nerve cells in such patients. However, the action of such DA agonists on the DA receptors also causes unwanted DA-ergic effects, such as nausea, vomiting and extrapyramidal effects, which can be debilitating and some DA agonists, such as apomorphine, are associated with further undesirable side-effects, especially when high doses are used, such as sedation, respiratory depression, hypotension, bradycardia, sweating and yawning. The severity and nature of such side-effects can be affected by the mode of administration of the drug. For instance, studies involving apomorphine have investigated a variety of routes for administration of this drug. However, oral administration of apomorphine tablets has required high doses to achieve the necessary therapeutic effect, because apomorphine administered by this route undergoes extensive presystemic metabolism in the small intestine and/or liver (the first pass effect). Also, long-term studies involving such oral forms were stopped after 7-10 days due to unexplained rises in blood urea nitrogen. Sublingual administration of apomorphine tablets caused severe stomatitis on prolonged use with buccal mucosal ulceration in half the patients treated. Intranasal administration produced transient nasal blockage, burning sensation and swollen nose and lips and, in some of the patients tested, had to be withdrawn because of what was considered to be chemical inflammation of the nasal mucosa.[1]

Accordingly, the only satisfactory way of administering apomorphine, which avoids high first pass metabolism, has been found to be subcutaneous administration and, thus, the only commercially available formulation of apomorphine is a liquid for subcutaneous injection or subcutaneous infusion. Even so, subcutaneous administration does not avoid the normal DA agonist side-effects, such as nausea and vomiting and subcutaneous administration, whether by injection or infusion, is not easy to accomplish, particularly by patients whose motor functions are already impaired, and therefore requires training of patients and caretakers. Also, the injection site must be changed every 12 hours to minimize risks of skin discoloration and nodules forming. In view of these problems, it is not surprising that the use of DA agonists, such as apomorphine, in the treatment of Parkinson's disease has been largely confined to the treatment of "off" periods caused by levodopa therapy despite the obvious clinical benefits of such drugs over levodopa.

It is apparent from the above that it would be highly desirable from a clinical point of view to find a way of administering DA agonists, such as apomorphine, which is easy for the patient to accomplish, therefore, reducing the need for supervision of administration and which bypasses first pass metabolism in the liver. In addition, such a formulation of apomorphine or of apomorphine prodrugs should have a more beneficial pharmacokinetic profile than apomorphine itself.[2-5]

Aporphine pro-drugs have been described and tested in animal models in the past.[6-21] Such pro-drugs have been mostly ester pro-drugs and di-symmetric, i.e. 10,11-di-esters. Thus, for instance, the following di-esters of aporphines have been described: di-acetyl, di-propionyl, dibutyryl, di-iso-butyryl, di-pivaloyl, di-pentanoyl, di-hexanoyl, di-hexadecanoyl, di-phenylacetyl, di-methoxyacetyl, di-trifluoroacetyl and di-heptafluorobutanoyl esters. Some reports of improved bio-availability of such esters have been presented, but the overall result was disappointing. As an example, the dipivaloyl ester pro-drug was much less active than the parent compound apomorphine itself. Due to the steric character of the pivaloyl group, it may be speculated that the ester hydrolysis of such a bulky group may be slower than for e.g. an acetyl group. 10,11-Di-acetyl-apomorphine is almost as potent as apomorphine itself.[6]

The possibility of preparing asymmetrical di-esters have been mentioned in U.S. Pat. No. 4,080,456.[11] Such asymmetrical di-esters were, however, not disclosed by means of specific working examples illustrating their preparation and characteristics and it was conceived by the inventors of that publication that such asymmetrical di-esters are difficult to make and that the pharmacology of such di-esters may be difficult to predict. Thus, all known di-acyl-aporphines actually prepared in practice are symmetrically substituted, i.e. the Same substituent is found on both the 10- and the 11-position of the aporphine skeleton. This is, of course, limiting with respect to optimalization of the physicochemical properties that are likely to be of importance for both transdermal and subcutaneous or intramuscular administration.

DISCLOSURE OF THE INVENTION

It is an object of the present invention to provide new aporphine esters having an improved bioavailability as compared to previously know aporphine esters.

It is another object of the present invention to provide new aporphine esters which have properties suitable for formulations for the administration via the transdermal, subcutaneous and intramuscular routes in order to achieve a longer duration of action against Parkinson's disease and other diseases.

It is still another object of the invention to provide transdermal and/or injectable formulations of aporphine pro-drugs by which the interval between the administrations can be increased considerably.

According to the present invention it was surprisingly found that aporphine mono- and asymmetrical di-esters have properties suitable for formulations for the administration via the transdermal, subcutaneous and the intramuscular route in order to achieve a longer duration of action of the therapeutic effect.

Thus, according to said finding, in one aspect the present invention provides a new aporphine derivative having the general formula (I).

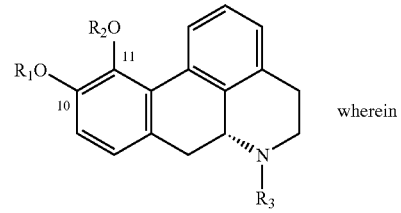

wherein one of $R_1$ and $R_2$ is hydrogen or acetyl and the other one is selected from the group consisting of $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl $(C_2-C_{16})$alkanoyl; aroyl which is unsubstituted or substituted by 1 to 3 substituents selected from the group consisting of halogen, cyano, trifluoromethanesulphonyloxy, $(C_1-C_3)$alkyl and $(C_1-C_3)$alkoxy, which latter may in turn be substituted by 1 to 3 halogen atoms; aryl$(C_2-C_{16})$alkanoyl which is unsubstituted or substituted in the aryl moiety by 1 to 3 substituents selected from the group consisting of halogen, $(C_1-C_3)$alkyl and $(C_1-C_3)$alkoxy, which latter may in turn be substituted by 1 to 3 halogen atoms; and hetero-arylalkanoyl having one to three heteroatoms selected from O, S and N in the heteroaryl moiety and 2 to 10 carbon atoms in the alkanoyl moiety and which is unsubstituted or substituted in the heteroaryl moiety by 1 to 3 substituents selected from the group consisting of halogen, cyano, trifluoromethane-sulphonyloxy, $(C_1-C_3)$ alkyl, and $(C_1-C_3)$alkoxy, which latter may in turn be substituted by 1 to 3 halogen atoms; and $R_3$ is selected from the group consisting of hydrogen; $(C_1-C_4)$-alkyl, which is unsubstituted or substituted by 1 to 3 halogen atoms; cyclopropyl and cyclopropylmethyl, and the physiologically acceptable salts thereof.

According to a preferred embodiment of the present invention there is provided an aporphine derivative of the general formula I above, wherein one of $R_1$ and $R_2$ is hydrogen or acetyl and the other one is selected from the group consisting of $(C_3-C_{20})$alkanoyl, $(C_4-C_7)$cycloalkanoyl, benzoyl which is unsubstituted or substituted by a chlorine atom or 1 to 3 methoxy groups, phenylacetyl which may be substituted with a chlorine atom, and heteroarylacetyl, and $R_3$ is $(C_1-C_3)$alkyl or cyclopropyl.

According to a more preferred embodiment of the present invention there is provided an aporphine derivative of the general formula I above, wherein one of $R_1$ and $R_2$ is hydrogen and the other one is selected from the group consisting of propanoyl, propenoyl, butanoyl, isobutanoyl, pivaloyl, decanoyl, hexadecanoyl, cyclopropanoyl and benzoyl and $R_3$ is methyl or propyl.

According to another more preferred embodiment of the present invention there is provided an aporphine derivative of the general formula I above, wherein one of $R_1$ and $R_2$ is acetyl and the other one is selected from the group consisting of butanoyl, isobutanoyl, cyclopropanoyl, cyclohexanoyl, pivaloyl, decanoyland hexadecanoyl and $R_3$ is methyl.

With regard to the definition of each symbol $R_1$, $R_2$ and $R_3$ in the formula I the following meanings should apply:

The terms "halo" and "halogen" are used to designate fluorine, chlorine, bromine and iodine, preferably fluorine and chlorine.

The term "$(C_3-C_{20})$alkanoyl" is used to designate the residue of a saturated aliphatic carboxylic acid of 3 to 20 carbon atoms, the carbon chain of which may be straight or branched. Examples of such alkanoyl groups are e.g. propanoyl, isopropanoyl, butanoyl, 2-methylpropanoyl, pentanoyl, 3-methyl-butanoyl, pivaloyl, n-hexanoyl, n-heptanoyl, n-octanoyl, n-nonanoyl, n-decanoyl, palmitoyl, stearoyl and eicosanoyl.

The term "halo-$(C_3-C_{20})$alkanoyl" is used to designate a $(C_3-C_{20})$alkanoyl group as defined above which is substituted by at least one halogen atom, preferably by 1 to 3 halogen atoms.

The term "$(C_3-C_{20})$alkenoyl" is used to designate the residue of an aliphatic carboxylic acid of 3 to 20 carbon atoms, the carbon chain of which may be straight or branched and which contains 1 to 3 conjugated or non-conjugated double-bonds. Examples of such alkenoyl groups are, e.g. acryloyl, methacryloyl, linoleoyl and linolenoyl.

The term "$(C_4-C_7)$cycloalkanoyl" is used to designate a group having the formula

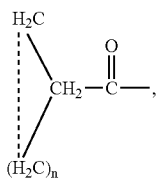

wherein n is an integer 1 to 4.

Such groups include cyclopropanoyl, cyclobutanoyl, cyclopentanoyl and cyclohexanoyl.

The term "$(C_3-C_6)$cycloalkyl-$(C_2-C_{16})$alkanoyl" is used to designate a group having the formula

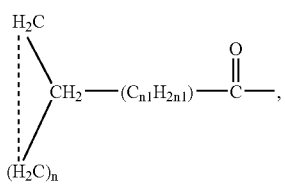

wherein n is defined as above, n is an integer 1 to 15. and the alkylene chain $(C_{n1}H_{2n1})$ may be straight or branched.

Examples of such groups are, e.g. cyclopropyl acetyl, cyclohexyl acetyl, cyclopropyl hexanoyl and cyclopropyl palmitoyl.

The term "aroyl" is used to designate bensoyl, 1-naphthoyl and 2-naphthoyl. Said aroyl group is unsubstituted or substituted by 1 to 3 substituents selected from the group consisting of halogen, cyano, trifluoromethanesulphonyloxy, $(C_1-C_3)$-alkyl and $(C_1-C_3)$alkoxy, which alkyl and alkyxoy groups in turn may be substituted by 1 to 3 halogen atoms. Examples of such substituted aroyl groups are m-methoxybenzoyl, p-trifluoromethoxybenzoyl, p-chlorobenzoyl, 3,4,5-trimethoxy-benzoyl, p-cyanobenzoyl and 3-chloro-1-naphtuoyl.

The term "$(C_1-C_3)$alkyl" is used to designate methyl, ethyl, propyl and isopropyl and the term "$(C_1-C_3)$alkoxy" is used to designate methoxy, ethoxy, propoxy and isopropoxy.

The term "aryl-$(C_2-C_{16})$alkanoyl" is used to designate a group of the formula

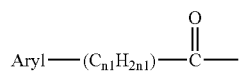

wherein Aryl and $n_1$ are as previously defined and the alkylene chain $(C_{n1}H_{2n1})$ may be straight or branched. The aryl moiety of said group may be substituted with substituents as indicated in connection with the aroyl groups above. Examples of aryl-$(C_2-C_{16})$alkanoyl groups are phenacetyl, p-chlorophenylacetyl, p-trifluoromethoxyphenylacetyl and phenylhexanoyl.

Examples of hetero-arylalkanoyl groups having one to three heteroatoms selected from O, S and N in the hetero-aryl moiety and 2 to 10 carbon atoms in the alkanoyl moiety and which are unsubstituted or substituted in the hetero-aryl moiety as indicated above are thiophen-2-yl-acetyl and pyrid-4-yl-hexanoyl.

The term "$(C_1-C_4)$alkyl" in the meaning of $R_3$ is used to designate a straight or branched alkyl group of 1 to 4 carbon atoms including methyl, ethyl, propyl, isopropyl, butyl, 1-methyl propyl, 2-methyl propyl and t-butyl.

According to another aspect of the invention there is provided processes for the preparation of compounds of the general formula (I) above.

Accordingly there is provided a process for the preparation of an aporphine mono-ester derivative having the general formula (I')

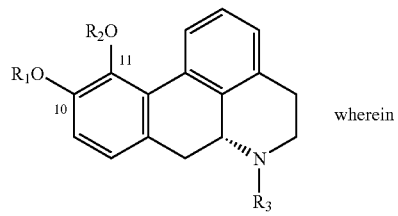

wherein one of $R_{11}$ and $R_{12}$ is hydrogen and the other one is selected from the group consisting of acetyl, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl $(C_2-C_{16})$alkanoyl; aroyl which is unsubstituted or substituted by 1 to 3 substituents selected from the group consisting of halogen, cyano, trifluoromethanesulphonyloxy, $(C_1-C_3)$alkyl and $(C_1-C_3)$alkoxy, which latter may in turn be substituted by 1 to 3 halogen atoms; aryl$(C_2-C_{16})$alkanoyl which is unsubstituted or substituted in the aryl moiety by 1 to 3 substituents selected from the group consisting of halogen, $(C_1-C_3)$alkyl and $(C_1-C_3)$alkoxy, which latter may in turn be substituted by 1 to 3 halogen atoms; and hetero-arylalkanoyl having one to three heteroatoms selected from O, S and N in the heteroaryl moiety and 2 to 10 carbon atoms in the alkanoyl moiety and which is unsubstituted or substituted in the heteroaryl moiety by 1 to 3 substituents selected from the group consisting of halogen, cyano, trifluoromethane-sulphonyloxy, $(C_1-C_3)$alkyl, and $(C_1-C_3)$alkoxy, which latter may in turn be substituted by 1 to 3 halogen atoms; and $R_3$ is selected from the group consisting of hydrogen; $(C_1-C_4)$-alkyl, which is unsubstituted or substituted by 1 to 3 halogen atoms; cyclopropyl and cyclopropylmethyl; which process comprises a) reacting an aporphine of the general formula (II),

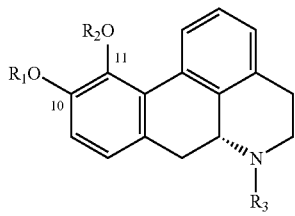

wherein $R_3$ is defined as above, with an acid chloride of the general formula (III)

$R_4-Cl$ wherein $R_4$ is as defined for said other one of $R'_1$ and $R'_2$ above, in the molar ratio of aporphine to acid chloride of from 1:1 to 1:5 and in trifluoroacetic acid and methylene chloride ($CH_2Cl_2$);

b) after the reaction being completed, evaporating the solvents or lyophilizing the reaction mixture;

c) dissolving the residual crude product mixture in $CH_2Cl_2$ and purifying by cromatography on $Al_2O_3$ eluting with $CH_2Cl_2$ and then with t-BuOH:$CH_2Cl_2$ or EtOH:$CH_2C_2$ mixtures in a stepwise gradient of increasing concentration of t-BuOH and EtOH, respectively, of from 1 to 15% by volume, preferably from 2 to 10% by volume, of the mixture, and isolating fractions containing the isomeric mono-ester derivatives of the formula (I'); and d) separating said isomeric mono-ester derivatives of formula (I') by known techniques to isolate a single mono-ester of the formula (I').

According to the present invention there is also provided a process for the preparation of an aporphine di-ester derivative having the general formula (I")

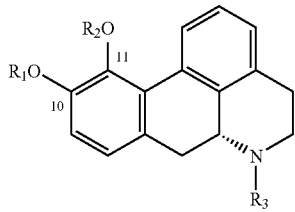

wherein one of $R''_1$ and $R''_2$ is acetyl and the other one is selected from the group consisting of $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl $(C_2-C_{16})$alkanoyl; aroyl which is unsubstituted or substituted by 1 to 3 substituents selected from the group consisting of halogen, cyano, trifluoromethanesulphonyloxy, $(C_1-C_3)$alkyl and $(C_1-C_3)$alkoxy, which latter may in turn be substituted by 1 to 3 halogen atoms; aryl($C_2-C_{16}$)alkanoyl which is unsubstituted or substituted in the aryl moiety by 1 to 3 substituents selected from the group consisting of halogen, $(C_1-C_3)$alkyl and $(C_1-C_3)$alkoxy, which latter may in turn be substituted by 1 to 3 halogen atoms; and hetero-arylalkanoyl having one to three heteroatoms selected from 0, S and N in the heteroaryl moiety and 2 to 10 carbon atoms in the alkanoyl moiety and which is unsubstituted or substituted in the heteroaryl moiety by 1 to 3 substituents selected from the group consisting of halogen, cyano, trifluoromethane-sulphonyloxy, $(C_1-C_3)$alkyl, and $(C_1-C_3)$alkoxy, which latter may in turn be substituted by 1 to 3 halogen atoms; and $R_3$ is selected from the group consisting of hydrogen; $(C_1-C_4)$-alkyl, which is unsubstituted or substituted by 1 to 3 halogen atoms; cyclopropyl and cyclopropylmethyl; which process comprises a) reacting an aporphine mono-ester of the general formula (I')

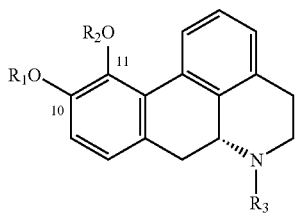 wherein one of $R'_1$ and $R'_2$ is hydrogen and the other one is acetyl and $R_3$ is as defined above, with an acid chloride of the general formula (IV)

$R_5-Cl$ wherein $R_5$ is as defined for said other one of $R''_1$ and $R''_2$ above, in the molar ratio of aporphine mono-ester to acid chloride of from 1:1 to 1:5 and trifluoroacetic acid and methylene chloride ($CH_2Cl_2$);

b) after the reaction being completed, evaporating the solvents or lyophilizing the reaction mixture;

c) dissolving the residual crude product mixture in $CH_2Cl_2$ and purifying by cromatography on $Al_2O_3$ eluting with $CH_2Cl_2$ and then with t-BuOH:$CH_2Cl_2$ or EtOH:$CH_2Cl_2$ mixtures in a stepwise gradient of increasing concentration of t-BuOH and EtOH, respectively, of from 1 to 15% by volume, preferably from 2 to 10% by volume, of the mixture, and isolating fractions containing the isomeric di-ester derivatives of the formula (I'); and d) separating said isomeric di-ester derivatives of formula (I") by known techniques to isolate a single di-ester of the formula (I").

In a first modification of the method for the preparation of an aporphine di-ester derivative having the general formula (I") as defined above a mono-ester of the general formula (I'), wherein $R'_1$ and $R'_2$ are as defined in connection with said formula except that neither thereof is acetyl, is reacted with acetyl chloride in a step a) in the molar ratio of aporphine mono-ester to acetyl chloride of from 1:1 to 1:5 and trifluoroacetic acid and methylene chloride ($CH_2Cl_2$), whereafter steps b) to d) as above follows.

In another modification of the method for the preparation of an aporphine di-ester derivative having the general formula (I") as defined above a mono-ester of the general formula (I'), wherein R'$_1$ and R'$_2$ are as defined in connection with said formula except that neither thereof is acetyl, is reacted in a step a) with acetic acid anhydride in CH$_2$Cl$_2$ in the presence of a basic catalyst such as triethylamine or pyridine whereafter steps b) to d) as above follows.

Alternatively, an aporphine mono-acetyl ester is reacted with the anhydride of an acid of the formula (V)

wherein R$_5$ is as defined above, in a step a) in CH$_2$Cl$_2$ in the presence of a basic catalyst such as triethylamine or pyridine whereafter steps b) to d) as above follows.

Aporphines, being catechols, are very sensitive to oxidation (e.g. in atmospheric air). This is especially true under basic conditions (a basic solution of apomorphine turns green to blue to violet to black in air). It is thus virtually impossible to handle such aporphines in the free base form, without the addition of antioxidants.

In addition, the pro-drugs of the present invention are designed to be easily hydrolyzed, making it difficult to use SiO$_2$ and nucleophilic alcohols for purification of the aporphine esters of the invention via column chromatography.

In step a) of the processes according to the present invention the esterification of the aporphines and the mono-acetyl ester of aporphines, respectively, is performed under acidic conditions in trifluoracetic acid (CF$_3$COOH) diluted with methylene chloride (CH$_2$Cl$_2$), a suitable dilution ratio being about 3-10 times. The acid chloride, possibly dissolved in CH$_2$Cl$_2$, is added to the aporphine or aporphine mono-acetyl ester, respectively, at a molar ratio between aporphine or aporphine mono-ester to acid chloride of from 1:1 to 1:5. The optimal ratio will vary depending on the steric properties of the acid chloride but will generally be within the range of from 1:1 to 1:2.

The reaction can be monitored by means of TLC (Al$_2$O$_3$ and eluting with CH$_2$Cl$_2$ or CH$_2$Cl$_2$:t-BuOH mixtures or CH$_2$Cl$_2$:EtOH mixtures).

After the reaction has become complete (generally within 1-24 h, depending on the acid chloride and molar ratio used) the solvents are evaporated from the reaction mixture or the reaction mixture is lyophilized in step b) of the processes of the invention. Evaporation of the solvents is generally carried out under reduced pressure.

For purification according to step c) of the processes of the present invention the residual crude product mixture from step b) is, in step c) dissolved in CH$_2$Cl$_2$ and purified by chromatography on Al$_2$O$_3$, elution being carried out by using first CH$_2$Cl$_2$ and then with mixtures of t-BuOH and CH$_2$Cl$_2$ in a stepwise gradient of increasing concentration of t-BuOH of from 1 to 15% by volume of t-BuOH calculated on the mixture, preferably from 2 to 10% by volume, for instance in steps of 1.0, 2.0, 5.0 and 10%. During the elution fractions containing the desired isomeric ester derivatives are collected. In case of the preparation of mono-esters, starting from an aporphine, potentially formed di-symmetric esters, will elute first and the mono-ester isomers (10-ester, 11-OH and 10-OH, 11-ester) thereafter. Unreacted aporphine (which is a catechol) will stick to the column. The isomeric mono-esters may hen be separated using known techniques such as flash chroatography, preparative HPLC (High Performance Liquid Chromaography), crystallization and other methods known per se. However, some of the isomeric mono-esters may prove difficult to separate and in such a case the mixture of the two isomers may be used as the starting material for the preparation of asymmetric di-esters or as the active principle in a pharmaceutical preparation.

In case of the preparation of the asymmetric di-esters, starting from an individual mono-ester isomer, the asymmetric di-esters will elute first and unreacted mono-esters thereafter.

Also in this case, when starting from a mixture of the two possible isomers of the mono-ester resulting from the esterification process of the present invention, the two di-ester isomers may prove difficult to separate and so it may appear advantageous to use the mixture of isomers as the active principle in a pharmaceutical preparation rather than taking the cost for the separation of the isomers.

According to a further aspect of the present invention there is provided a pharmaceutical composition comprising, as an active principle, at least one aporphine derivative of formula I as defined above or a physiologically acceptable salt thereof together with a pharmaceutically acceptable carrier, diluent or excipient.

The term "at least one" as used in the paragraph next above is primarily meant to refer to the case when the mixture of two isomers resulting from the esterification process of the present invention is difficult to separate and hence it might appear advantageous to use said mixture rather than a single isomer. It might also appear advantageous to use the mixture of the two isomers or a combination of two compounds according to the invention having different combinations of the meanings of the symbols R$_1$ and R$_2$ in formula I between each other.

The aporphine ester pro-drugs of formula I according to the invention may be incorporated in the pharmaceutical composition according to the invention as the base or as an acid addition salt, especially the hydrochloride salt. Other suitable salts are those formed by the acids HBr and sulphonic acids like methanesulphonic acid, octanesulphonic acid and hexadecansulphonic acid.

From the discussion in the section Background art it is apparent that there is a need for improved ways of administration for apomorphine and/or apomorphine pro-drugs, which are not well absorbed orally and/or are targets for extensive first pass elimination. According to the present invention it was surprisingly found that a dosage form with a prolonged duration of action can be achieved by using aporphine pro-drugs of formula I according to the invention suspended (as a neat oil or as crystals, or dissolved in a suitable and pharmaceutically acceptable solvent (e.g. water, ethanol, DMSO, i-PrOH or benzylbenzoate)) in a pharmaceutically acceptable depot oil (e.g. viscoleo, sesame oil or olive oil) and injected subcutaneously or intramuscularly with a syringe or a "pen injector". Alternatively, these drugs may, in a suitable composition and with a suitable vehicle (penetration enhancer), be applied to a patch for transdermal administration. The composition could include also a local anesthetic (e.g. lidocaine) to avoid injection pain, in particular at intramuscular injections.

Thus, according to a preferred embodiment of the pharmaceutical composition of the present invention said composition is in the form of a patch or an ointment for transdermal administration. Said patch or ointment preferably also comprises stabilizers, solubilizers and permeation activators to facilitate the passage of the active principle through the skin.

According to another preferred embodiment of the composition according to the present invention said composition is in the form of a depot preparation for subcutaneous or intramuscular administration comprising said aporphine derivative of formula I or the physiologically acceptable salt thereof dissolved or suspended in an oil. As indicated above such a composition preferably, in addition to the aporphine derivative of formula I or the physiologically acceptable salt thereof, contains a local anesthetic.

An injectable depot formulation is a dosage form, which is generally intended to have a therapeutic activity for 2 to 4 weeks after administration (e.g. neuroleptics like Fluphenazine decanoate in sesame oil). In order to maintain effective drug plasma levels the dosage form should release the drug at a more or less constant rate during the desired dosing interval. The actual working principle to obtain this prolonged drug release is rather simple. Since the drug substance has to reach the systemic circulation to display its effect, most depot injection systems decrease the transport rate of the drug from the site of injection to the circulation. The subcutaneous route of administration avoids the problem of the first pass effect, which is very crucial in the case of Apomorphine, which is a catechol and is thus sensitive for oxidation, conjugation and COMT inactivation. Apomorphine can not be given orally due to extensive first pass metabolization.

A suitable form of depot preparation is the subcutaneous or intramuscular administration of an oil solution and/or oil suspension of a lipophilic drug. This gives a slow transport over the oil-biofluid interface and a slow dissolution in the biophase. Thus, when the drug is dissolved in an a polar solvent (e.g. oils), which is non-miscible with the aqueous biological fluids, the drug has to be transported over the oil/water interface. When the oil/water partition coefficient is high, the transport will be slow. For very lipophilic drugs, the release from the oil phase may last for up to several weeks.

The maximum volume of an oil solution/suspension to be injected intramuscularly or subcutaneously is 2-4 mL. This is feasible for the preparations of the aporphine derivatives of the present invention. The accumulated daily dose used in apomorphine s.c. therapy in Parkinson's disease is 4-10 times about 1-4 mg (4-40 mg/day). For the animal experiments performed in the pharmacological research, which led to the present invention, ca 2 mg Apomorphine×HCl (or equivalent molar amount of compounds according to Formula I above, as the base or as a suitable salt or ion-pair) was dissolved in 1 mL of an oil (sesame oil, Viscoleo or another approved oil) and the mixture was gently heated (max 50° C.) shaken in a test tube shaker and ultrasonicated for a short time (minutes) until the mixture became a homogeneous solution or suspension. If necessary, the test compound was first dissolved in 50-300 μL DMSO, water, t-BuOH, PEG, benzylbenzoate, or another suitable and approved solvent or mixtures thereof, before adding the oil (see above) to a total volume of 1 mL.

Other suitable administration forms for the aporphine derivatives of formula I according to the invention include forms suited for oral, sublingual, pulmonary, rectal, vaginal or intraduodenal administration.

A preferred form of a pharmaceutical composition intended for oral administration is one which is provided with an enteric coating which is quickly dissolved in the duodenum/small intestine.

Such a form may comprise a tablet core prepared by compressing a mixture of active ingredient(s), excipients, adjuvants and possible other additives which core is then provided with an enteric coating.

Alternatively such a form may comprise a mixture of active ingredient(s) and appropriate excipients and adjuvants enclosed in a capsule dissolving in duodenum/small testine and thus functioning as an enteric coating for said mixture. Preferably said mixture is in the form of a solution of the active ingredient(s) in a solvent.

It is preferred that the new aporphine ester pro-drugs of formula I according to the present invention are present in the composition in an amount from 0.05 to 100 mg, preferably 0.05 to 20 mg in each dosage unit. Where a high daily dose is required, this may be administered in several (lower dose) injections over the day. However, this still means fewer injections per day than with the presently used formulation with apomorphine×HCl in water (can reach 10-12 injections per day).

As mentioned above in the section Background art, DA agonists like apomorphine produce side-effects such as nausea and vomiting. It is therefore preferred that the composition of the invention is administered after, or in conjunction with, an anti-emetic, at least at the start of the therapy. The antiemetic may be conveniently administered in the same composition as the new aporphine ester pro-drugs of the present invention. Alternatively, the anti-emetic may be administered separately from the DA agonist by any of the usual oral or parenteral routes of administration, for instance, by tablets, capsules, suspensions, suppositories, infusions, injections, etc., at a suitable time which may be before, after or simultaneously with administration of the DA agonist. It is likely that, after an adaptation period, the anti-emetic may be taken away from the therapeutic scheme.

Thus according to a further preferred embodiment of the pharmaceutical composition according to the present invention, said composition, in addition to the aporphine derivative of formula I or the physiologically acceptable salt thereof contains an effective amount of an anti-emetic agent.

It is preferred that the anti-emetic is present in the composition in an amount of from 1 to 120 mg, more preferably 1-60 mg. However, the precise quantity of anti-emetic to be administered to the patient will depend on the anti-emetic that is selected. A well-known and much used anti-emetic is the peripheral DA antagonists 5-chloro-1-[1-[3-(2,3-dihydro-2-oxo-IH-benzimidazol-1-yl)propyll-4-piperidinyll-1,3-dihydro-2H-benzimidazol-2-one (domperidone) and salts thereof. Preferred daily dose range for the anti-emetic domperidone is 20-120 mg, more preferably 30-60 mg. Where a high daily dose is required, this may be administered in several units of smaller dose. Another anti-emetic is Naloxone, an apomorphine antidote for apomorphine's emetic effect.

For parenteral administration, fluid unit dosage forms are prepared utilizing a compound of formula I of the invention or a pharmaceutically acceptable salt thereof and a sterile vehicle. The compound, depending on the vehicle and concentration used, can be either suspended or dissolved in the vehicle. In preparing solutions, the compound can be dissolved for injection and filter sterilized before filling into a suitable vial or ampoule and sealing. Advantageously, adjuvants such as local anaesthetic preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved and sterilization cannot be accomplished by filtration. Possibly, a surfactant or wetting agent is included in the composition to facilitate a uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 100 mg, more suitably 0.05 to 20.0 mg, for example 0.2 to 5 mg; and such unit doses may be administered more than once a day; for example two or three times a day, so that the total daily dosage is in the range of about 0.5 to 100 mg; and such therapy may extend for a number of weeks, months, years, including the rest of the patient's life.

Other diseases/conditions, beside Parkinson's disease, which can be treated with aporphine pro-drugs of the present invention and in the formulation of the present invention are restless legs syndrome (RLS), hemicrania, erectile dysfunction (impotence in men) and also sexual stimulation in e.g. menopausal women (stimulation of vaginal lubrication and erection of clitoris), hyperprolactemia and psychoses (e.g. schizophrenia). The herewith mentioned diseases do not form a limitation to the present invention, thus, other diseased states involving the DA-ergic system may also be relevant for treatment with compounds of the present invention.

When administered in accordance with the invention, no unacceptable toxicological effects are expected with the compounds of the invention.

DA agonists, especially apomorphine, can be used to predict the likely response to levodopa in patients with Parkinson's disease. Accordingly, the present invention in a further aspect thereof provides the use of a pharmaceutical composition as defined above for use in the evaluation of Parkinson's disease.

In still another aspect of the present invention there is provided the use of an aporphine derivative of formula I as defined above for the manufacture of a medicament for the treatment of Parkinson's disease, hemicrania, restless legs syndrome (RLS), sexual dysfunction in men and women, hyperprolactemia and psychotic disorders, and/or evaluation of Parkinson's disease.

According to one aspect of the best mode contemplated at present for carrying out the invention, the pharmaceutical composition is in a form suited for oral administration which is provided with an enteric coating which is quickly dissolved in the duodenum/small intestine.

According to another aspect of the best mode contemplated at present for carrying out the invention, the aporphine derivative is mono-butyryl apomorphine.

The invention will now be further described by means of a number of examples which are not to be construed as limiting the present invention.

EXAMPLES

Apparatuses and Analysis Methods

Melting points were determined in open glass capillaries on an Electrothermal digital melting-point apparatus and are uncorrected. Mass spectra were obtained on an Unicam 610 -Automass 150 GC-MS system, or on a PE-Sciex API 3000 triple quadrupole mass spectrometer (Sciex, Concord, Ont., Canada) equipped with a Turbo Ionspray interface. Progress of the reaction was followed on a Perkin-Elmer 8410 Gas Chromatograph equipped with a Cp Sil 5 Column. Free hydroxy groups of the products were derivatized with acetic anhydride or butyryl chloride. Column chromatography was performed with Aluminum Oxide 90 active neutral, starting with $CH_2Cl_2$ as eluents, and gradually increasing its polarity by adding tert-butanol up to 10% (v/v). Thin layer chromatography was performed on $Al_2O_3$ 60 F254 neutral plates.

Example 1

Mono-Acetyl Apomorphine

Apomorphine HCl (0.25 g, 0.83 mmol) was dissolved in $CH_2Cl_2$ (25 mL) and trifluoroacetic acid (2 mL). The mixture was stirred on ice. Acetyl chloride (0.13 g, 1.65 mmol) was added. The temperature slowly increased to room temperature. The reaction mixture was left overnight, and was then evaporated under reduced pressure, yielding a yellow oil. Purification by column chromatography yielded 17.4 mg (0.056 mmol, 6.8%) of gray crystals. API-MS: m/z 310 (M+H)+.

Example 2

Mono-Butyryl Apomorphine

Apomorphine HCl (0.25 g, 0.83 mmol) was dissolved in $CH_2Cl_2$ (25 mL) and trifluoroacetic acid (2 mL). The mixture was stirred on ice. Butyryl chloride (0.09 g, 0.83 mmol) was added. The temperature slowly increased to room temperature. After 3.5 hours, 0.5 equivalents of butyryl chloride was added. Another 0.5 equivalent was added after 5.5 hours. The reaction mixture was left overnight and was then evaporated under reduced pressure, yielding an yellow oil. Purification by column chromatography yielded the product as a colorless oil. Crystallization from hexane yielded 14 mg (0.042 mmol, 5.1%) of gray crystals: mp 99-102° C.; API-MS: m/z 338 (M+H)+.

Example 3

Mono-Pivaloyl Apomorphine

Apomorphine HCl (0.45 g, 1.49 mmol) was dissolved in $CH_2CL_2$ (25 mL) and trifluoro-acetic acid (2 mL). The mixture was stirred on ice. Pivaloyl chloride (0.54 g, 4.46 mmol) was added. The temperature slowly increased to room temperature. The reaction mixture was left overnight, and was then evaporated under reduced pressure, yielding an yellow oil. Purification by column chromatography yielded the product as a colorless oil. Crystallization from hexane yielded 114 mg (0.32 mmol, 21.8%) of gray crystals: mp 128-130° C.; API-MS: m/z 0.393 (M+).

Example 4

Mono-Hexadecanoyl Apomorphine

Theoretical yield: 98 mg (base)

Synthesis 1: Apomorphine×HCl (50.0 mg; 0.164 mmol) was dissolved in $CF_3COOH$ (0.3 mL) and one equivalent (0.164 mmol; 45.1 mg=49.7 µL) of hexadecanoyl chloride was added in one batch at room temperature. TCL ($Al_2O_3$; $CH_2Cl_2$:EtOH 9:1 or 5:1 was checked at different times).

First 2 eq. were added and after a night at room temperature the solvent was evaporated and the residue was redissolved in $CH_2Cl_2$ and a sample was taken with a pipette and chromatographed on a pipette filled with $Al_2O_3$. Elution was performed with first $CH_2Cl_2$ and then with $CH_2Cl_2$:EtOH (9:1). The isolated product (fraction 17, 5 mg) was dissolved in Viscoleo and one normal rat in a dose of 10 mg/kg (corresponds to ca 5 mg/kg ApoxHCl) s.c. in the neck. Clear signs of dopaminergic activity for a very long time (ca 24 h).

It was believed that the initial reaction was incomplete and therefore another 3 eqv. were added. It looked as if this brought the reaction to completion. After chromatography (see above) the isolated product (15 mg) was dissolved in Viscoleo and so injected into two rats (ca 3.7 mg/kg; corr. to 2 mg/kg of ApoxHCl) in a concentration of 3.7 mg/mL. No effect whatsoever was found.

Explanation: The first small batch contained both mono- and di-C16-Apo and obviously displayed activity when injected in Viscoleo. The second batch contained only di-C16-Apo, which is obviously not (or very slowly) hydrolyzing in vivo completely to Apo itself. Therefore, a new batch was started and the reaction controlled by API Ms.

Synthesis 2: The same reaction was set up, thus a 50 mg batch. This time 1 eqv. was added and the reaction was checked and found incomplete. However, no di-C16 had yet formed. Thus, another eqv. was added and API Ms showed ca 60%, 100% and 10% of Apo, mono-C16-Apo and di-C16-Apo, respectively. It was decided the reaction was stopped at this stage and the solvent ($CF_3COOH$) was evaporated. The residue was dissolved in ca 1 mL $CH_2Cl_2$ and put on a pipette $Al_2O_3$ column and eluted with $CH_2Cl_2$ and then $CH_2Cl_2$:EtOH (9:1). Fractions 28-31 were analyzed with API Ms and were shown to contain ca 50/50 of Apo and mono-C16-Apo, despite the fact that the Apo put on the column should be held tightly by $Al_2O_3$! Therefore, to fractions 28-31 was added one drop of pyridine and thereafter one drop of Ac20 for acetylation of any free OH group in the fractions. Very surprisingly, no di-Ac-Apo was found in the API Ms samples! Thus, no Apo is present in these samples after chromatography. Apo must have been formed in the samples diluted with MeOH in preparation for the API Ms runs. Mono-C16-Apo is thus very sensitive to methanolysis (and probably to hydrolysis) and should not come in contact with nucleophilic alcohols like MeOH and EtOH! However, a non-nucleophilic alcohol like t-BuOH should be OK!

The rest of the batch was put onto a $Al_2O_3$ (ca 5 g) column and eluted with $CH_2Cl_2$ and then $CH_2Cl_2$:EtOAc in increasing EtOAc concentrations. However, no distinct fractions containing the product were seen. Thus, a mixture of $CH_2Cl_2$:t-BuOH (9:1) was applied and a spot was observed in fractions 53 and 54, which were pooled leaving only 4.5 mg of a fluorescent product, which was confirmed on API Ms to be mono-hexadecanoyl apomorphine.

Examples 5 to 18

In analogy to the procedure of Examples 1 to 4 further apomorphine mono-esters were prepared using the appropriate acid chlorides.

The mono-esters prepared in Examples 1 to 18 and analysis data are summarized in the following Table 1.

TABLE 1

| Example No. | Acid used | [M + H]$^+$ of mono-ester |
| --- | --- | --- |
| 1 | Acetyl chloride | 310 |
| 2 | Buturyl chloride | 338 |
| 3 | Pivaloyl chloride | 352 |
| 4 | Hexadecanoyl chloride | 506 |
| 5 | Propionyl chloride | 324 |
| 6 | Decanoyl chloride | 422 |
| 7 | Isobuturyl chloride | 338 |
| 8 | Propenoyl chloride | 322 |

TABLE 1-continued

| Example No. | Acid used | [M + H]$^+$ of mono-ester |
| --- | --- | --- |
| 9 | Cyclopropanoyl chloride | 336 |
| 10 | Cyclohexanoyl chloride | 378 |
| 11 | Benzoyl chloride | 372 |
| 12 | Phenylacetyl chloride | 386 |
| 13 | o-Methoxybenzoyl chloride | 402 |
| 14 | p-Trifluormethoxybenzoyl chloride | 456 |
| 15 | p-Chlorobenzoyl chloride | 406 |
| 16 | p-Chlorophenylacetyl chloride | 420 |
| 17 | 3,4,5-Trimethoxybenzoyl chloride | 462 |
| 18 | 2-Thiophenylacetyl chloride | 392 |

Examples 19 to 23

Asymmetric di-esters of apomorphine were prepared in a two-step process using in each step a methodology analogous to that of Examples 1 to 18.

In the first step 15 mM apomorphine was reacted with acetyl chloride in TFA to give a mixture of the 10,11-isomeric mono-acetyl apomorphines. In the second step, in each example an acid chloride as set forth in Table 2, below, was added. Table 2 also gives analysis data for the products thus prepared.

| Example No. | Acid chloride in the 2:nd step | [M + H]$^+$ of product |
| --- | --- | --- |
| 19 | Buturyl chloride | 380 |
| 20 | Isobuturyl chloride | 380 |
| 21 | Cyclopropanoyl chloride | 378 |
| 22 | Hexadecanoyl chloride | 548 |
| 23 | Pivaloyl chloride | 394 |

Example 24

ApomorphinexHCl (50 mg, 165 µmol) was dissolved in ca 0.5 mL $CF_3COOH$ and pivaloylchloride (4 eqv., 660 µmmol, 4×19.8 mg or µL=79.2 µL) was added at 0° C. After ca 5 min the ice bath was removed and the temperature was allowed to reach room temperature and the reaction was allowed to stir over night. The volatiles were removed on the rotavapor under reduced pressure and the remaining oil was dissolved in $CH_2Cl_2$:EtOH (20:1) and was applied to a $Al_2O_3$ (neutral) column (10-15 g) and was eluted with $CH_2Cl_2$:EtOH (20:1) and the pure fractions containing the mono-pivaloylated APO were collected (35 mg after evaporation of the solvents) and the mono-Piv-APO (10-Piv-APO or 11-Piv-APO) was documented with NMR (300 MHz) and MS (API, see Table 1).

The collected product (35 mg) was dissolved in ca 0.5 mL $CF_3COOH$ and acetylchloride (ca 2 eqv. of the starting amount APOxHCl (i.e. 165×2=330 µmol=2×12.9=25.8 µL) was added at room temperature. The volatiles were evaporated and the remaining oil was dissolved in CH2Cl2 and was applied to a $Al_2O_3$ (neutral) column and the products were eluted with first $CH_2Cl_2$ and then with $CH_2Cl_2$:EtOH (20:1). The fractions containing the two isomers of piv, Ac-APO were taken to NMR (fraction 45) and to biological testing (fraction 46; 6.5 mg and fraction 47; 1.5 mg). GC/MS was documented for fractions 45-47 and gave the following relationships between the isomers: fraction 45 first peak/second peak=75/25; fraction 46: 67/33 and fraction 47: 83/17, respectively.

Example 25

Apomorphine×HCl (50 mg, 165 µmol) was dissolved in ca 0.5 mL $CF_3COOH$ and propionylchloride (4 eqv., 660 µmol, 3×15.2 mg or µL=45.6/1.4 µL=32.6 µL) was added at room temperature. TLC on $Al_2O_3$ in $CH_2Cl_2$ and $CH_2C_2$/EtOH (20:1) shows that there is probably too much propionyl chloride added (major product was di-propionyl). Despite this fact, 2 eqv. of acetyl chloride were added, without first separating, to convert unreacted propionyl-apo to acetyl, propionyl-apo.

After a night in room temperature, the volatiles were evaporated and the remaining oil was dissolved in $CH_2Cl_2$ and was applied to an $Al_2O_3$ (neutral) column and the products were eluted with first $CH_2Cl_2$ and then with $CH_2Cl_2$:EtOH (20:1). The fractions containing the two isomers of propionyl, Ac-APO and the di-propionyl-Apo were taken to NMR and to biological testing. These fractions contained ca 95% of the di-propionyl-Apo and ca 5% of the mixed isomers propionyl, Ac-Apo. GC/MS was documented and showed two small peaks for the di-symmetric isomers and a big peak for the di-propionyl-Apo.

Examples 26-29

By a procedure analogous to that of Example 24 further asymmetric diesters of apomorphine were prepared using in the first step an acid chloride as set forth in Table 3 below. In the second step reaction with acetyl chloride was performed. Table 3 also gives analysis data for the products thus prepared.

TABLE 3

| Example No. | Acid chloride in the 1:st step | $[M + H]^+$ of product |
|---|---|---|
| 24 | Buturyl chloride | 380 |
| 25 | Isobuturyl chloride | 380 |
| 26 | Isopropanoyl chloride | 378 |
| 27 | Hexadecanoyl chloride | 548 |

Examples 28-35

By a procedure analogous to that of Examples 1-18 but using R(−)-propylnorapomorphine as starting material rather than apomorphine a further series of mono-esters were obtained.

Thus 5 mM R(−)-propylnorapomorphine in dichlormethane containing 3% TFA was reacted with the respective acid chlorides set forth in Table 4 below to obtain the corresponding mono-ester isomers as a mixture. Table 4 also gives analysis data for the products thus prepared.

TABLE 4

| Example No. | Acid chloride used | $[M + H]^+$ of product |
|---|---|---|
| 28 | Acetyl chloride | 338 |
| 29 | Propanoyl chloride | 352 |
| 30 | Cyclopropanoyl chloride | 364 |
| 31 | Buturyl chloride | 366 |
| 32 | Isobuturyl chloride | 366 |
| 33 | Pivaloyl chloride | 380 |
| 34 | Decanoyl chloride | 450 |
| 35 | Hexadecanoyl chloride | 534 |

Examples 36-43

Using the reaction mixtures obtained according to Examples 28-35 as starting materials for the reaction with acetyl chloride in analogy to the procedure of Examples 19 to 28 a further series of asymmetric di-esters were prepared. Table 5 below states the different starting materials and gives analysis data for the products thus prepared.

TABLE 5

| Example No. | Starting material from Ex. No. | $[M + H]^+$ of product |
|---|---|---|
| 36 | 28 | 380 |
| 37 | 29 | 394 |
| 38 | 30 | 406 |
| 39 | 31 | 408 |
| 40 | 32 | 408 |
| 41 | 33 | 422 |
| 42 | 34 | 492 |
| 43 | 35 | 576 |

Formulation Example

Preparation of a depot dosage form of aporphine esters of the present invention in oil.

An aporphine ester of the present invention, as the free base or as the salt, is ideally directly dissolved in a pharmaceutically accepted oil (see below) or first dissolved or suspended in a suitable solvent like an alcohol (e.g. t-BuOH) or in DMSO, PEG etc., and this solution is, thereafter, dissolved or suspended in a suitable oil (e.g. sesame oil, Viscoleo, olive oil, walnut oil). An antioxidant may also be included in order to protect the formulation from oxidative degradation. After appropriate sterilization (autocalve, gamma-irradiation, ethylene oxide, sterile filtration etc.), the solution (mixture, suspension) is stored in the freezer until use. Before use, the solution should aquire room temperature and then be shaken vigorously before injecting the solution or suspension subcutaneously (s.c.) or intramuscularly (i.m.).

Due to the potential nausea and emesis induced by apomorphine, naive subjects may be pre-treated with an anti-emetic like domperidone. After a period of treatment, such domperidone therapy is likely to be redundant due to the patients' adaptation to apomorphine.

Preferably, each portion or designated unit dosage form contains from 0.5 to 20 mg or aporphine esters of the present invention (or an equivalent amount of the salt/ion-pair), more preferably from 0.5 to 15 mg and especially 1 mg.

Pharmacokinetic Studies

Protocol for the Determination of Apomorphine in Plasma

Apparatuses

The samples were analyzed offline with an RP-HPLC with an electrochemical detector. The system comprised of an ANTEC electrochemical detector, a C-18 column, a GILSON 231 sampler injector and a GILSON 401 Diluter, a PHARM CIA HPLC pump 2150, and Kipp en Zonen flatbed recorder. The flow was 0.25 mL/min.

The mobile phase was:
2000 mL UP
860 mL methanol
34 g citric acid monohydrate
13.5 g $NaHPO_3*2H_2O$
1.43 g EDTA 25 mg/L OSA
1 mM TMA The solvent your was ultra filtered (UP).

Animals

The test animals used were male albino Wistar rats weighing between 200 and 370 g. Food and water were available to the rats all the time. They were set in a normal 12 hour day night rhythm. Before the operation the animals resided in a larger cage with a group of rats. During the experiments they were alone in a cage with the dimensions 25*25*35 cm. The blood sampling was performed in freely moving animals, which were all conscious. In this way potential behavioral changes from the treatment could be registered. The operation consisted of the application of a cannula in the vena jugularis. After an experiment the rats were given at least 24 hours to recover.

Sampling and Extraction of Blood

Through a jugularis cannula, blood was taken from the freely moving rats. This took place with an injection syringe and a PE-tubing with the diameter of 0.75 mm.
1. the sampling times were: t=0, 15, 30, 60, 120, 240, 480, 720 and 1440 minutes.
2. in Eppendorf test tubes, 10 µL of 0.35% mercapto ethanol and 10 µL of 10% EDTA was spiked (final concentration mercapto ethanol is 0.01%).
3. 0.35 mL of blood was collected in the Eppendorf test tubes (see under 2 above).
4. the blood collected was centrifuged for five minutes at 22° C. and 3500 rounds per minute.
5. 200 µL of plasma was pipetted off and transferred into clean test tubes.
6. these test tubes were stored at minus 18° C. until a analyzed.

Extraction of Plasma

To the plasma was added a solution containing 500 ng/mL NPA (N-Propyl-norapomorphine). NPA is the internal standard with a final concentration of 50 ng/mL. Additionally, on 100 µL of a 1% solution of sodium hydrogen carbonate (NaHCO$_3$) was added.
1. 3 mL of diethylether (P.A. quality) was added with a glass pipette.
2. all test tubes where shaken for three minutes on a Multivortex shaker.
3. the test tubes were centrifuged for 15 minutes at 4° C. and 1000 rounds per minute.
4. the ether layer was pipetted off and brought to another test tube.
5. ether extraction was performed three times.
6. the ether layers (9 mL in total) was evaporated with warm water and nitrogen gas flowing over the surface.
7. the remains in the test tubes, after the evaporation of the ether, were dissolved in 100 µL of the mobile phase.
8. the samples were vortexed and then put in to the centrifuge.
9. the samples prepared were subjected to analysis on the HPLC system.

Transdermal Experiment in One Single Rat

About 5 mg of apomorphine mono-Bu ester prepared according to Example 2 was dissolved in about 120 mg of Fenuril hand cream (PNU). This amount of cream was applied with a spatula on the shaved neck of the rat, weighing about 350 g. Dopaminergic effects were seen but they were weak in their appearance.

These effects were monitored for about one hour and consisted in exploratory behavior and grooming and chewing in the beginning phase. After about half an hour the rats became sedated and was mostly sitting still with intermittent sniffing and chewing and some yawning.

After one hour and 10 minutes, about five droplets of DMSO were smeared on to the rat neck. After about 10 minutes, intense jawning, sniffing, penile licking and chewing was registered. About 30 minutes after DMSO, the rat became very active with sniffing chewing and licking and displayed a typical dopaminergic syndrome including locomotor activity. The stereotypy lasted for at least two hours. After another two hours (in total 4 hours), the rat was sitting still in an awkward position, sitting rather high on its four legs. Thus, the rat was not in the normal lying position and was easily activated by turning the cage. Chewing sniffing and yawning were still observed at this time (t=ca 6 h).

The next day at 10:00 a.m. the rat was still active showing signs of chewing. This was not a normal behavior and should be the effect of small amounts of a apomorphine still circulating in the blood of the rat.

In a comparative experiment 7 mg of Apomorphine hydrochloride solid was dissolved in DMSO (70 microliters). The solid material dissolved immediately and 20 microliters, corresponding to 2 mg of Apomorphine hydrochloride salt, was applied to the shaved rat neck. After about 10 to 15 minutes signs of chewing and sniffing were observed. The rat became a bit sedated (due to the presynaptic effect of the drug) but continued sniffing and chewing. After about 30 minutes the rat displayed stereotypy. After about two hours of intense stereotypy, including sniffing local motor activity rearing and chewing, rather abruptly, the rat stopped. After this time, the rat mostly lay down to rest. No other signs of dopaminergic activity were registered after this time.

REFERENCES (1) Zaleska, B.; Domzal, T. Neurol. Neurochir. Pol. 1999, 33, 1297-1303.
(2) van Laar, T.; van der Geest, R.; Danhof, M.; Bodde, H. E.; Goossens, P. H.; Roos, R. A. Clin. Neuropharmacol. 1998, 21, 152-158.
(3) Gancher, S.; Nutt, J.; Woodward, W. Mov. Disord. 1991, 6(3): 212-216.
(4) Pietz, K.; Hagell, P.; Odin, P. J. Neurol. Neurosurg. Psychiatry 1998, 65, 709-716.
(5) Nutt, J. G.; Carter, J. H. Neurology 2000, 54, 247-250.
(6) Atkinson, E. R.; Battista, S. P.; Ary, I. E.; Richardson, D. G.; Harris, L. S.; Dewey, W. L. J. Pharm. Sci. 1976, 65, 1682-1685.
(7) Baldessarini, R. J.; Walton, K. G.; Borgman, R. J. Neuropharmacology 1976, 15, 471-478.
(8) Baldessarini, R. J.; Boyd, A. E., III,; Kula, N. S.; Borgman, R. J. Psychoneruoendocrinology 1979, 4, 173-175.
(9) Burov, Y. V.; Zagorevskii, V. A.; Varkov, A. I.; Sipiliina, N. M.; Ivanova, T. I. Khim.-Farm. Zh. 1985, 19, 1192-1194.
(10) Hinshaw, W. B., Jr.; Pearl, J. 21 pp. 1975.
(11) Seidelmann, D.; Schmiechen, R.; Horowski, R.; Kehr, W.; Palenschat, D.; Paschelke, G. U.S. Pat. No. 4,080,456.
(12) Tye, N. C.; Horsman, L.; Wright, F. C.; Large, B. T.; Pullar, I. A. Eur. J. Pharmacol. 1977, 45, 87-90.
(13) Baldessarini, R. J.; Walton, K. G.; Borgman, R. J. Neuropharmacology 1975, 14, 725-731.
(14) Borgman, R. J.; Baldessarini, R. J.; Walton, K. G. J. Med. Chem. 1976, 19, 717-719.
(15) Borgman, R. J. Neuropharmacology 1976, 15, 471-478.

(16) Di Renzo, G. F.; Amoroso, S.; Basile, V.; Quattrone, A.; Annunziato, L. IRCS Med. Sci.: Libr. Compend. 1982, 10, 822.
(17) Scatton, B.; Worms, P. Naunyn-Schmiedeberg's Arch. Pharmacol. 1978, 303, 271-278.
(18) Scatton, B.; Worms, P. J. Pharm. Pharmacol. 1979, 31, 861-863.
(19) Worms, P.; Scatton, B. Eur. J. Pharmcol. 1977, 45, 395-396.
(20) Zijlstra, S.; Visser, G. M.; Korf, J.; Vaalburg, W. Appl. Radiat. Isot. 1993, 44, 651-658.
(21) Zijlstra, S.; De Groot, T. J.; Kok, L. P.; Visser, G. M.; Vaalburg, W. J. J. Org. Chem. 1993, 58, 1643-1645.

The invention claimed is:

1. An aporphine derivative having the general formula (I)

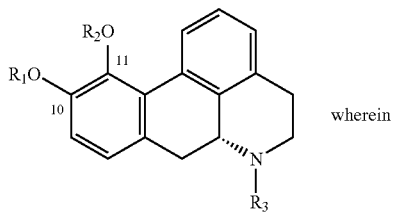

wherein one of $R_1$ and $R_2$ is hydrogen or acetyl and the other one is a $(C_3-C_{20})$ alkanoyl, a $(C_3-C_{20})$alkenoyl, a $(C_4-C_7)$ cycloalkanoyl, or benzoyl; and $R_3$ is selected from the group consisting of hydrogen; $(C_1-C_4)$-alkyl, which is unsubstituted or substituted by 1 to 3 halogen atoms; cyclopropyl and cyclopropylmethyl, and the physiologically acceptable salts thereof.

2. An aporphine derivative according to claim 1, wherein $R_3$ is $(C_1-C_3)$ alkyl or cyclopropyl.

3. An aporphine derivative according to claim 2, wherein one of $R_1$ and $R_2$ is hydrogen and the other one is selected from the group consisting of propanoyl, propenoyl, butanoyl, iso-butanoyl, pivaloyl, decanoyl, hexadecanoyl, cyclopropanoyl and benzoyl and $R_3$ is methyl or propyl.

4. An aporphine derivative according to claim 2, wherein one of $R_1$ and $R_2$ is hydrogen and the other one is selected from the group consisting of butanoyl, isobutanoyl, cyclopropanoyl, cyclohexanoyl, pivaloyl, decanoyl and hexadecanoyl and $R_3$ is methyl.

5. An aporphine derivative according to claim 2, wherein one of one of $R_1$ and $R_2$ is hydrogen and the other one is pivaloyl and $R_3$ is methyl.

6. Process for the preparation of an aporphine mono-ester derivative having the general formula (I')

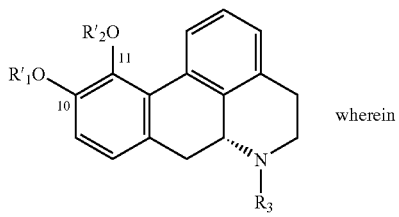

wherein one of $R'_1$ and $R'_2$ is hydrogen and the other one is a $(C_3-C_{20})$alkanoyl, a $(C_3-C_{20})$alkenoyl, or a $(C_4-C_7)$ cycloalkanoyl; and $R_3$ is selected from the group consisting of hydrogen; $(C_1-C_4)$-alkyl, which is unsubstituted or substituted by 1 to 3 halogen atoms; cyclopropyl and cyclopropylmethyl; which process comprises a) reacting an aporphine of the general formula (II),

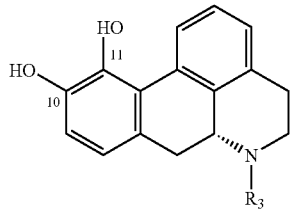

wherein $R_3$ is defined as above, with an acid chloride of the general formula (III)

$R_4$-Cl wherein $R_4$ is as defined for said other one of $R'_1$ and $R'_2$ above, in the molar ratio of aporphine to acid chloride of from 1:1 to 1:5 and in trifluoracetic acid and methylene chloride ($CH_2Cl_2$);

b) after the reaction being completed, evaporating the solvents or lyophilizing the reaction mixture;

c) dissolving the residual crude product mixture in $CH_2Cl_2$ and purifying by chromatography on $Al_2O_3$ eluting with $CH_2Cl_2$ and then with t-BuOH:$CH_2Cl_2$ or EtOH:$CH_2Cl_2$ mixtures in a stepwise gradient of increasing concentration of t-BuOH and EtOH, respectively, of from 1 to 15% by volume of the mixture, and isolating fractions containing the isomeric mono-ester derivatives of the formula (I'); and d) separating said isomeric mono-ester derivatives of formula (I') by known techniques to isolate a single mono-ester of the formula (I').

7. The process according to claim 6, wherein one of one of $R'_1$ and $R'_2$ is hydrogen and the other one is pivaloyl and $R_3$ is methyl.

8. The process according to claim 7, wherein said dissolving the residual crude product mixture in $CH_2Cl_2$ and purifying by chromatography on $Al_2O_3$ eluting with $CH_2Cl_2$ and then with t-BuOH:$CH_2Cl_2$ or EtOH:$CH_2Cl_2$ mixtures in a stepwise gradient of increasing concentration of t-BuOH and EtOH, respectively, of from 2 to 10% by volume, of the mixture, and isolating fractions containing the isomeric mono-ester derivatives of the formula (I').

9. A pharmaceutical composition comprising as an active principle at least one aporphine derivative of formula I as identified in claim 1 or a physiologically acceptable salt thereof together with a pharmaceutically acceptable carrier, diluent or excipient.

10. A pharmaceutical composition according to claim 9, which is in the form of a patch or ointment for transdermal administration.

11. A pharmaceutical composition according to claim 10, which furthermore comprises stabilizers, solubilizers and permeation activators to facilitate the passage of the active principle through the skin.

12. A pharmaceutical composition according to claim 9, which is in the form of a depot preparation for subcutaneous or intramuscular administration comprising said aporphine derivative of formula I or the physiologically acceptable salt thereof dissolved or suspended in an oil.

13. A pharmaceutical composition according to claim 12, which in addition to the aporphine derivative of formula I or the physiologically acceptable salt thereof contains a local anesthetic.

14. A pharmaceutical composition according to claim 9, which is in a form suited for oral, sublingual, pulmonary, rectal, vaginal or intraduodenal administration.

15. A pharmaceutical composition according to claim 9, which in addition to the aporphine derivative of formula I or the physiologically acceptable salt thereof contains an effective amount of an anti-emetic agent.

16. A process for manufacturing a medicament, said process comprising contacting an aporphine derivative of formula I as identified in claim 1 or a physiologically acceptable derivative thereof with a pharmaceutically acceptable carrier.

17. Method for the treatment of Parkinson's disease comprising administering to a subject in need of such a treatment of a therapeutically effective amount of an aporphine derivative of the formula I as defined in claim 1 or of a physiologically acceptable salt thereof.

18. A pharmaceutical composition comprising as an active principle at least one aporphine derivative of formula I as identified in claim 5 or a physiologically acceptable salt thereof together with a pharmaceutically acceptable carrier, diluent or excipient.

19. A pharmaceutical composition according to claim 18, which is in the form of a patch or ointment for transdermal administration.

20. A pharmaceutical composition according to claim 19, which furthermore comprises stabilizers, solubilizers and permeation activators to facilitate the passage of the active principle through the skin.

21. A pharmaceutical composition according to claim 18, which is in the form of a depot preparation for subcutaneous or intramuscular administration comprising said aporphine derivative of formula I or the physiologically acceptable salt thereof dissolved or suspended in an oil.

22. A pharmaceutical composition according to claim 21, which in addition to the aporphine derivative of formula I or the physiologically acceptable salt thereof contains a local anesthetic.

23. A pharmaceutical composition according to claim 18, which is in a form suited for oral, sublingual, pulmonary, rectal, vaginal or intraduodenal administration.

24. A pharmaceutical composition according to claim 18, which in addition to the aporphine derivative of formula I or the physiologically acceptable salt thereof contains an effective amount of an anti-emetic agent.

25. A process for manufacturing a medicament, said process comprising contacting an aporphine derivative of formula I as identified in claim 5 or a physiologically acceptable derivative thereof with a pharmaceutically acceptable carrier.

26. Method for the treatment of Parkinson's disease comprising administering to a subject in need of such a treatment of a therapeutically effective amount of an aporphine derivative of the formula I as defined in claim 5 or of a physiologically acceptable salt thereof.

27. The aporphine derivative according to claim 1, wherein one of $R_1$ and $R_2$ is hydrogen or acetyl and the other one is a $(C_3$-$C_{20})$ alkanoyl.

28. The process according to claim 6, wherein one of $R'_1$ and $R'_2$ is hydrogen and the other one is a $(C_3$-$C_{20})$alkanoyl.

* * * * *